United States Patent
Jalde et al.

(10) Patent No.: US 8,527,036 B2
(45) Date of Patent: Sep. 3, 2013

(54) CATHETER POSITIONING METHOD AND COMPUTERIZED CONTROL UNIT FOR IMPLEMENTING THE METHOD

(75) Inventors: Fredrik Jalde, Bromma (SE); Joachim Saellvin, Saltsjoe-Boo (SE); Christer Sinderby, Toronto (CA)

(73) Assignee: Maquet Critical Care AB, Solna (SE)

( * ) Notice: Subject to any disclaimer, the term of this patent is extended or adjusted under 35 U.S.C. 154(b) by 1255 days.

(21) Appl. No.: 12/238,938

(22) Filed: Sep. 26, 2008

(65) Prior Publication Data
US 2009/0084382 A1    Apr. 2, 2009

(30) Foreign Application Priority Data
Sep. 28, 2007    (SE) ........................ 0702191

(51) Int. Cl.
*A61B 5/04* (2006.01)
*A61M 16/00* (2006.01)

(52) U.S. Cl.
USPC .............. 600/509; 600/380; 128/207.14

(58) Field of Classification Search
USPC ............... 600/300, 509, 380; 607/124; 128/207.14–207.17, 202.22, 204.23
See application file for complete search history.

(56) References Cited

U.S. PATENT DOCUMENTS

| | | | |
|---|---|---|---|
| 5,048,532 A | 9/1991 | Hickey | |
| 5,431,696 A * | 7/1995 | Atlee, III | 607/124 |
| 5,820,560 A | 10/1998 | Sinderby et al. | |
| 6,259,938 B1 * | 7/2001 | Zarychta et al. | 600/380 |
| 6,588,423 B1 | 7/2003 | Sinderby | |
| 7,273,056 B2 | 9/2007 | Wilson et al. | |
| 2010/0116274 A1 * | 5/2010 | Jalde | 128/204.23 |

FOREIGN PATENT DOCUMENTS
WO    WO 2005/115234    12/2005

OTHER PUBLICATIONS

"Predicting Internal Distance to the Stomach for Positioning Nasogastric and Orogastric Feeding Tubes in Children," Beckstrand et al, Journal of Advanced Nursing, vol. 59, No. 3 (2007) pp. 274-289).

* cited by examiner

*Primary Examiner* — Mark W Bockelman
(74) *Attorney, Agent, or Firm* — Schiff Hardin LLP

(57) ABSTRACT

A control unit for a ventilator is arranged to receive, from each of a number of electrode pairs on an esophageal catheter a bioelectric signal having an ECG component. The control unit has a calculating unit that determines the ECG component of each of the bioelectric signals and a position unit that determines the position of the catheter in relation to the patient's diaphragm based on a comparison the amplitudes of ECG components of the bioelectric signals.

10 Claims, 2 Drawing Sheets

CATHETER POSITIONING METHOD AND COMPUTERIZED CONTROL UNIT FOR IMPLEMENTING THE METHOD

BACKGROUND OF THE INVENTION

1. Field of the Invention

The present invention relates to a method of positioning a catheter in a patient's esophagus, a control unit for use with a ventilator, and a computer-readable medium encoded with programming instructions for use in such a control unit.

2. Description of the Prior Art

U.S. Pat. No. 5,671,752 discloses a method and a device for registering the myoelectrical activity of the diaphragm by means of an esophageal catheter having an array of electrodes. Such a signal from an esophageal catheter is prone to disturbances from other myoelectrical signals that are present in the patient's body. For improving the signal-to-noise ratio of such an electromyographic signal cross-correlation of the signals from the different electrode pairs in the catheter is used. Electrodes on opposite sides of the diaphragm but having approximately the same distance to the diaphragm will produce signals that are opposite but substantially equal in magnitude. By subtracting the signals from one electrode from the other the two desired signals will be added, while the noise components of the two signals will substantially cancel each other out.

When a patient is breathing spontaneously but still needs breathing support the myoelectric signal from the diaphragm can be used to control the ventilator. U.S. Pat. Nos. 5,820,560 and 6,588,423 both disclose methods and devices for triggering ventilatory support to a patient using a myoelectrical signal obtained from the diaphragm.

A problem when obtaining a myoelectrical signal from the diaphragm is positioning of the catheter within the patient's esophagus. To obtain a proper signal some of the electrodes should be placed above the diaphragm and some below it. There is a possibility that the catheter will be inserted too far, or not be inserted far enough. In both cases the catheter will detect a weak signal or may not capture any signal at all. The catheter may also capture myoelectrical signals from other muscles instead of, or in addition to, the signal from the diaphragm. Hence, it is difficult to obtain an optimal catheter position and the ventilator may have to work in pneumatic triggering mode if the signal is too weak.

Ensuring the correct positioning of the catheter within the patient is therefore important. Some methods for approximating how far the catheter should be inserted are known. For example the Xiphoid process involves measuring the distance between the bridge of the nose and the earlobe. Based on this distance the distance from the mouth or nose to the esophagogastric junction can be estimated. This is often referred to as NEX, or Nose to ear Xiphoidus measurements. This estimated distance can be used as an initial value when positioning the catheter in the esophagus of a patient. This is, however, only an estimate which may be more or less accurate depending on individual variations. This is discussed in the Journal of Advanced Nursing 2007 August; 59(3):274-289. For small children, and especially for premature babies, the distance may be estimated by measuring the circumference of the head. Such a method is disclosed, for example, in WO 2005/115234.

U.S. Pat. No. 6,259,938 discloses method of positioning the catheter by means of depth markings that can be used to gauge the distance the catheter has been inserted into the patient. In addition to the depth markings pressure detecting mechanisms that are spaced apart so that they can detect the esophageal and gastric pressures, to detect when a part of the catheter has reached the stomach.

WO 2006/049787 discloses a system for optically guiding a catheter having a light-emitting means using an external detection device that detects the transdermally projected light emitted by the light-emitting point from within the patient.

These known positioning methods are based on approximations and assumptions, for example, of the actual position of the diaphragm, which will vary from one patient to another. Therefore they cannot assume a precise position of the catheter.

SUMMARY OF THE INVENTION

An object of the present invention is to ensure correct positioning of an esophageal catheter that is to be used to record a myoelectric signal from the diaphragm of a patient.

This object is achieved in accordance with the invention by a method for positioning a catheter in a patient's esophagus, wherein the catheter has a number of electrodes for registering bioelectric signals, such as EMG signals, including the steps of inserting the catheter into the esophagus to a first position registering at least a first bioelectric signal and a second bioelectric signal with at least a first electrode pair and a second electrode pair of the catheter, the bioelectric signals containing an ECG component, determining the ECG component of each of the bioelectric signals, comparing the respective ECG components of the bioelectric signals of the electrode pairs, and determining the position of the catheter in relation to the patient's diaphragm based on the comparison.

The object is also achieved in accordance with the invention by a control unit for a ventilator configured to receive signals from a number of electrodes on an esophageal catheter, the control unit having inputs configured to receive, from each of at least two electrode pairs on the catheter, a bioelectric signal containing an ECG component, and the control unit being having a calculating module that determines the ECG component of each of the at least two bioelectric signals, a position for determining module that determines the position of the catheter in relation to the patient's diaphragm based on a comparison the amplitudes of ECG components of the bioelectric signals.

The object is also achieved by a computer-readable medium for use in a computerized control unit for a ventilator, that is encodes with computer readable instructions that, when executed in the control unit cause the control unit to receive first and second bioelectric signals from at least first and second electrode pairs, respectively, of a catheter, each of the bioelectric signals containing an ECG component, determine the ECG component of each of the bioelectric signals, compare the ECG components of the bioelectric signals of the at least two electrode pairs, and determine the position of the catheter in relation to the patient's diaphragm based on the comparison.

By registering the damping of the ECG signal between pairs of electrodes the actual position of the diaphragm will be taken into account. This is because the diaphragm will cause a significant damping of the ECG signal so that electrodes positioned above the diaphragm will register a higher amplitude of the disturbing ECG signal than electrodes below the diaphragm.

Using the inventive method it may be ensured that the esophageal catheter is positioned with some electrodes above and some below the diaphragm. Such a positioning of the catheter is desirable for providing a reliable EMG signal related to the activity of the diaphragm. According to the invention, therefore, the positioning does not have to be based on the EMG signal, but can be based entirely on the ECG signal, which is a strong bioelectric signal, and its behavior near the diaphragm.

Preferably, the two adjacent electrode pairs having the largest difference in ECG amplitude are determined to be the closest electrode pairs to the patient's diaphragm. This is because the diaphragm will cause a significant damping of the ECG amplitude between the electrode pair located just above the diaphragm and the electrode pair located just below the diaphragm.

The method may further include the steps of changing the position of the catheter within the esophagus to a second position and, in the second position, registering a bioelectric signal from each of at least two pairs of electrodes of the catheter, each of the bioelectric signals containing an ECG component, determining the amplitude of the ECG component of each of the bioelectric signals, and determining the position of the catheter in relation the patient's diaphragm based on the amplitudes of ECG components determined in said first and second positions.

This enables the comparison between two different positions of the catheter, which may provide more complete information about the position of the diaphragm.

To ensure that only the ECG component is used for determining the position, any P-wave contained in the ECG signals may be filtered out before determining the amplitudes of the ECG components.

A threshold value may be set, such that the position of the catheter in the patient's diaphragm will be determined by the calculation means only if the amplitudes of ECG signals recorded by two electrode pairs differ by more than a predetermined threshold. This will help to avoid an erroneous determination that the catheter is correctly positioned, for example, if the whole catheter is positioned on one side of the diaphragm.

The programming instructions of the computer-readable medium may also cause the control unit to present the determined position of the catheter to a user on a display, for example, the display of the ventilator. This will assist the operator in positioning the catheter correctly.

DESCRIPTION OF THE PREFERRED EMBODIMENTS

Figure 1:
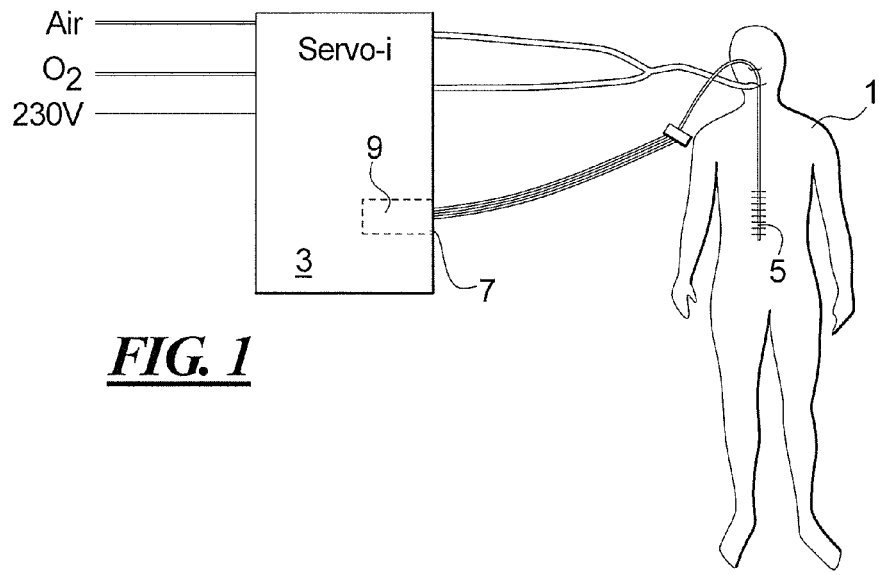
FIG. 1 illustrates a patient with an esophageal catheter used to control a ventilator.

FIG. 1 is a schematic overview of a patient 1 connected to a ventilator 3 and having an esophageal catheter 5 inserted in order to record a myoelectric signal from the diaphragm. This myoelectric signal is fed to a control input 7 of the ventilator 3 to control the ventilating function of the patient 1. The catheter 5 has a number of electrodes, for example, nine electrodes placed equidistantly in an array along the catheter to produce 8 sub-signals, each sub-signal being a difference signal between two neighboring electrodes. The sub-signals will be processed in a control unit 9 in the ventilator to produce the overall signal that can be used to control the ventilator. To this end, the control unit 9 is operated by at least one computer program product used to control the ventilator to perform the calculations and other relevant functions of the inventive method.

If the catheter position is approximately correct, each of the sub-signals described above also contain an electrocardiographic (ECG) signal component since the electrodes will inevitably pick up the heart activity. An electrode that is positioned above the diaphragm the ECG component will detect a higher amplitude of the ECG signal than an electrode that is positioned below the diaphragm, since the diaphragm will cause a significant damping of the ECG signal amplitude.

The damping between the electrode pairs may be determined in a number of different ways. For example the difference between the peak-to-peak ECG values for each electrode pair may be used. Alternatively the signal may be integrated to obtain the area, or the root mean square of the ECG signal at each electrode pair may be determined. The actual manner of determining the damping is not essential.

When the P-wave amplitude is bigger than the amplitude of the QRS complex, it may be necessary to be able to separate the damping of the P-wave amplitude from the damping of the total ECG amplitude. The P-wave amplitude often decreases rapidly with the distance between the electrode pair and the atrium. Thus there may be a big amplitude decrease above the diaphragm and another big amplitude decrease further down the electrode array caused by the diaphragm. To distinguish the damping of the P-wave and the damping of the total ECG amplitude, it must be taken into account that the P-wave amplitude often decreases rapidly above the diaphragm.

Starting at the lower end of the electrode array, a correctly placed electrode array will have a low ECG amplitude on the electrode pairs close to the stomach, a significant increase of the amplitude at the electrode pairs placed above the diaphragm, and then, in some cases, an additional increase of the ECG amplitude for the upper electrode pairs placed close to the atrium caused by a strong P-wave. However, in many cases the P-wave amplitude is non-existent, or minor, compared to the amplitude of the QRS complex.

According to the invention the position of the diaphragm is detected by measuring the eight electrode pairs continuously or with short time intervals, calculating the ECG amplitude on each electrode pair and comparing the calculated ECG amplitudes for all electrode pairs. According to the invention then the biggest amplitude difference, damping, between at least two electrode pairs is determined. The comparison of the electrodes may be implemented according to the following exemplary embodiment.

Starting at the lower end, the tip of the catheter, and going upwardly along the electrode array, a relatively low ECG amplitude on the lower electrode pairs is ascertained. The respective ECG amplitudes of the lowest and second lowest electrode pairs are compared, then the second and third lowest, and so on. The first significant increase of ECG amplitude along the array is thereby determined.

Figure 2:
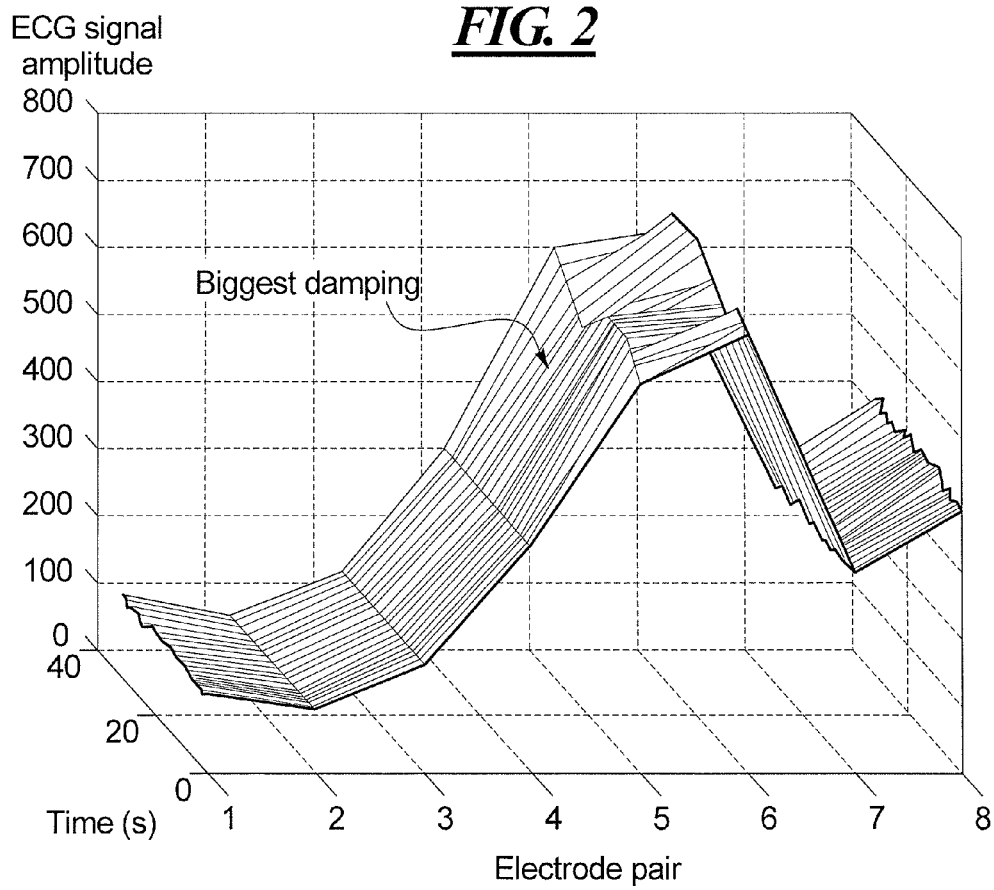
FIG. 2 illustrates the ECG signal amplitude as a function of time and electrode pair.

FIG. 2 illustrates the variation in the ECG amplitude recorded by each of the electrode pairs. The electrode pairs are numbered 1-8, the pair designated 1 being the pair formed by the two first electrodes inserted into the patient, and the pair designated 8 being the pair formed by the two last electrodes inserted into the patient, that is, the uppermost electrode pair. As can be seen, the ECG signal amplitude varies between the electrode pairs. In the example of FIG. 2 the biggest difference between two neighboring electrode pairs is found between pairs 4 and 5. Alternatively, the highest damping between combinations of three neighboring electrode pairs may be considered. It might be assumed that the amplitude should vary in the same direction between all electrode pairs, that is, that the amplitude recorded by electrode pair number 1 should be higher than that of pair number 2, which should in turn be higher than that of pair number 3, etc. That this is not always the case is caused by other factors. For example, the P-wave, if present, might have an impact on the overall ECG amplitude.

The initial positioning of the catheter, before executing the inventive method, should be made as precisely as possible. Preferably, most of the electrodes should be positioned below the diaphragm when starting the positioning according to the invention to avoid confusing the P-wave with the ECG signal. Therefore, it is recommended to use an estimated positioning method for the initial positioning. Examples of such methods, for example the NEX method, are discussed in the background section above.

Figure 3:
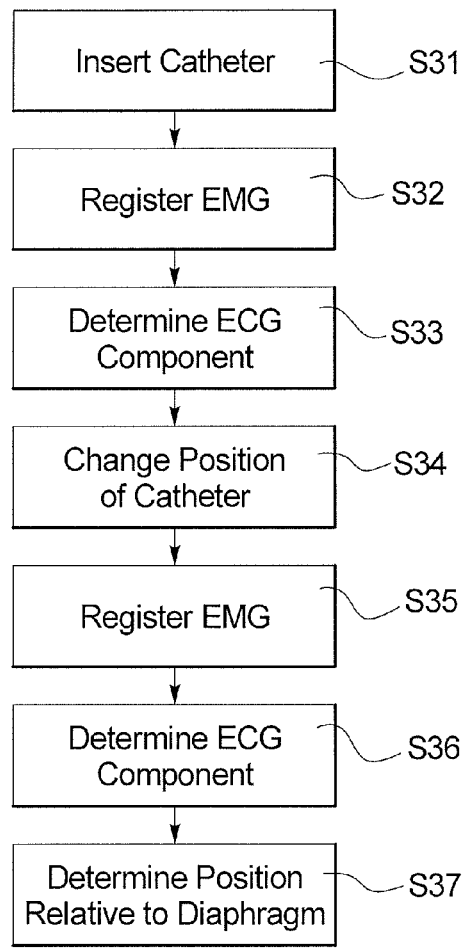
FIG. 3 is a flowchart of an embodiment of a method of determining the position of the catheter relative to the diaphragm in accordance with the invention.

In order to detect the correct position a simple registration of the signals from all electrode pairs may suffice. FIG. 3 illustrates a more elaborate method of optimizing the positioning of the electrodes relative to the catheter:

Step S31: Insert the catheter. To assist in inserting the catheter, preferably an approximate positioning method, such as NEX, is used. Alternatively, the depth may be estimated based on experience. Preferably, the catheter is first inserted a bit less deep than the measured or estimated depth.

Step S32: Register the bioelectric signals over each of the electrode pairs. These bioelectric signals will comprise an ECG component.

Step S33: Determine the ECG component of the bioelectric signal over each of the electrode pairs. This is typically done in the control unit 9.

Step S34: Change the position of the catheter. If the catheter was inserted to less that the estimated depth in step S31, this involves inserting the catheter a bit deeper, for example, a distance corresponding to the distance between two electrode pairs, or twice that distance, deeper into the patient.

Step S35: Register the bioelectric signals over each of the electrode pairs. These bioelectric signals will comprise an ECG component.

Step S36: Determine the ECG component of the bioelectric signal over each of the electrode pairs. This is typically done in the control unit 9.

Steps S35 and S36 may be repeated as many times as desired for different positions of the catheter, to produce different signals for comparison.

Step S37: When at least two sets of ECG signals have been determined the position of the electrodes relative to the diaphragm for each of the depths can be determined. Based on this an appropriate location of the catheter can be achieved.

Figure 4:
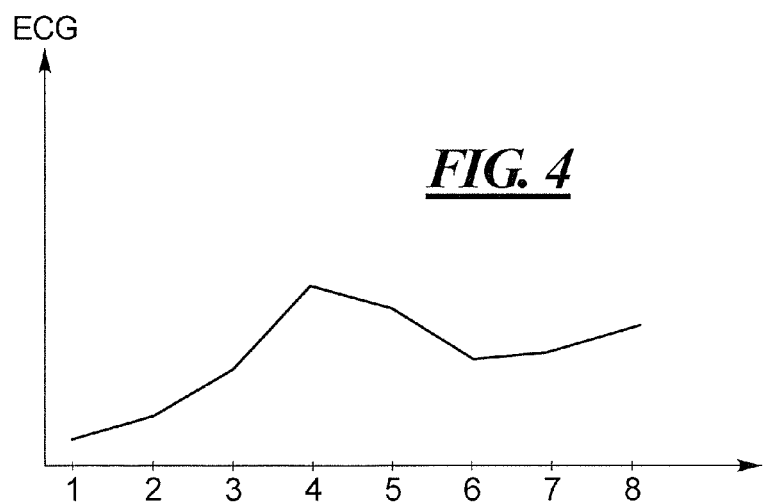
FIG. 4 is an example of a user interface for displaying information related to the inventive method.

The result of the comparison of the ECG amplitudes from the different electrode pairs may be presented to the operator in any suitable way, for example as shown in FIG. 4. FIG. 4 is essentially a two-dimensional representation of a curve similar to the one shown in FIG. 2, intended solely as an example.

As in FIG. 2, the positions of eight electrode pairs 1-8 are marked along the X-axis, 1 being the first electrode pair inserted into the patient and 8 being the upper-most electrode pair. The Y-axis represents the amplitude of the ECG signal component for each electrode pair. As can be seen, the difference between the ECG amplitudes recorded by adjacent electrode pairs that is the damping of the ECG signal between adjacent electrode pairs, varies. In this example, the largest difference is found between electrode pairs number three and four, which means that the diaphragm is located between electrode pairs three and four in this case. Typically, immediately above the diaphragm the ECG component will drop again.

The inventive method may be combined with several conditions. For example, a requirement may be that the ECG amplitude is lower for the electrodes having lower numbers than for the electrodes having higher numbers. A minimum level for the difference may be set to ensure that the difference is actually caused by the damping of the diaphragm and not merely by, for example, the increasing distance from the heart.

It is also possible to filter out the P-wave before processing the ECG signal to ensure that the ECG amplitude registered is actually the amplitude of the QRS wave. Techniques to filter out the P-wave are well known in the art.

Although modifications and changes may be suggested by those skilled in the art, it is the intention of the inventors to embody within the patent warranted hereon all changes and modifications as reasonably and properly come within the scope of their contribution to the art.

We claim as our invention:

1. A control unit for a ventilator comprising:
   control unit inputs configured to receive at least a first bioelectric signal and a second bioelectric signal respectively from at least a first electrode pair and a second electrode pair on a catheter, each signal comprising an ECG component; and
   a programmable calculating unit configured to access stored programming instructions and to operate according to the accessed programming instructions to determine the ECG component of each of the at least two bioelectric signals and a programmable position determining unit that is also configured to access stored programming instructions and to operate according to the accessed programming instructions to determine the position of the catheter in relation to the patient's diaphragm based on a comparison of respective amplitudes of ECG components of the first and second bioelectric signals, and to make a signal available in electronic form at an output of said programmable position determining unit that indicates said position of the catheter in relation to the patient's diaphragm.

2. A control unit according to claim 1, wherein the calculating unit is configured to operate according to the accessed programming instructions to determine the position of the catheter in the patient's diaphragm only if the respective amplitudes of ECG signals recorded by two electrode pairs differ by more than a predetermined threshold.

3. A control unit according to claim 1, wherein the calculating unit, via said control unit inputs, receives, from each of at least two electrode pairs on the catheter, a bioelectric signal at at least two different points in time, each comprising an ECG component, and is configured to operate according to the accessed programming instructions to determine the ECG component of each of the at least two bioelectric signals and to determine the position of the catheter in the patient's diaphragm received at each of the at least two different points in time, and to determine the position of the catheter in relation the patient's diaphragm based on the amplitudes of ECG components determined in said first and second points in time.

4. The control unit as claimed in claim 1 wherein each of said ECG components comprises a portion thereof representing a P-wave, and wherein said programmable position determining unit is configured to filter said portion representing a P-wave out of each of said ECG components before making said comparison of respective amplitudes of ECG components of the first and second bioelectric signals.

5. A ventilator comprising:
a breathing assist unit configured to interact with a patient via an esophageal catheter inserted in a first position in the esophagus;
said catheter comprising a plurality of electrodes that register bioelectric signals; and
a control unit having inputs connected to said electrodes to receive at least a first bioelectric signal and a second bioelectric signal respectively from a first electrode pair and second electrode pair, each of said bioelectric signals comprising an ECG component, said control unit comprising a programmable calculating unit configured to access stored programming instructions and to operate according to the accessed programming instructions to determine the ECG component of the respective first and second bioelectric signals, and a programmable position determining unit that is also configured to access stored programming instructions and to operate according to the accessed programming instructions to determine a position of the catheter in relation to the patient's diaphragm based on a comparison of respective amplitudes of the ECG components of the first and second bioelectric signals, and to make a signal available in electronic form at an output of said programmable position determining unit that indicates said position of the catheter in relation to the patient's diaphragm.

6. A ventilator as claimed in claim 5 wherein each of said ECG components comprises a portion thereof representing a P-wave, and wherein said programmable positioning determining unit is configured to filter said portion representing a P-wave out of each of said ECG components before making said comparison of respective amplitudes of ECG components of the first and second bioelectric signals.

7. A ventilator as claimed in claim 5 comprising a display in communication with said control unit, said display being supplied with said electronic signal from said output of said position determining unit and displaying a visual representation of the determined position of the catheter in relation to the patient's diaphragm, as indicated by said electronic signal.

8. A non-transitory computer-readable storage medium encoded with programming instructions for use in a control unit of a ventilator, said programming instructions, when executed by the control unit, causing the control unit to:
receive a first bioelectric signal and a second bioelectric signal from at least a first electrode pair and a second electrode pair, respectively, of a catheter positioned in the esophagus of patient, each of said bioelectric signals comprising an ECG component;
determine, by executing the programming instructions, the ECG component of each of the bioelectric signals;
compare, by executing the programming instructions, the ECG components of the bioelectric signals;
determine, by executing the programming instructions, the position of the catheter in relation to the patient's diaphragm based on the comparison; and
make an electronic signal, indicating said position of the catheter in relation to the patient's diaphragm, available at an output of the control unit.

9. A non-transitory computer-readable storage medium as claimed in claim 8 wherein said programming instructions cause said control unit to present the determined position of the catheter in relation to the patient's diaphragm, as indicated by said electronic signal, on a display.

10. A non-transitory, computer-readable storage medium as claimed in claim 8 wherein each ECG component comprises a portion thereof representing a P-wave, and wherein said programming instructions further cause said control unit to:
filter said portion of each ECG component representing a P-wave out of each of the ECG components before comparing the ECG components of the bioelectric signals.

* * * * *